United States Patent
Toga et al.

(10) Patent No.: US 10,837,051 B2
(45) Date of Patent: Nov. 17, 2020

(54) ENZYME REACTION REAGENT HAVING DRIED FORM AND METHOD FOR PREPARING THE SAME

(71) Applicant: Kaneka Corporation, Osaka (JP)

(72) Inventors: Tatsuya Toga, Hyogo (JP); Shigehiko Miyamoto, Hyogo (JP); Hozumi Tanaka, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 230 days.

(21) Appl. No.: 15/806,395

(22) Filed: Nov. 8, 2017

(65) Prior Publication Data

US 2018/0057857 A1    Mar. 1, 2018

Related U.S. Application Data

(63) Continuation of application No. PCT/JP2013/063648, filed on May 6, 2016.

(30) Foreign Application Priority Data

May 8, 2015   (JP) .................. 2015-095535

(51) Int. Cl.
| | | |
|---|---|---|
| *C12Q 1/68* | (2018.01) | |
| *C12Q 1/686* | (2018.01) | |
| *C12Q 1/48* | (2006.01) | |
| *C12Q 1/6806* | (2018.01) | |
| *C01C 1/24* | (2006.01) | |
| *C07C 215/04* | (2006.01) | |
| *C07C 229/04* | (2006.01) | |

(52) U.S. Cl.
CPC ............... *C12Q 1/686* (2013.01); *C01C 1/24* (2013.01); *C07C 215/04* (2013.01); *C07C 229/04* (2013.01); *C12Q 1/48* (2013.01); *C12Q 1/6806* (2013.01); *C12Q 2527/125* (2013.01); *C12Q 2563/137* (2013.01)

(58) Field of Classification Search
CPC ..................................................... C12Q 1/686
USPC ......................................................... 435/6.12
See application file for complete search history.

(56) References Cited

FOREIGN PATENT DOCUMENTS

| EP | 072631 A1 | 8/1996 |
|---|---|---|
| EP | 2682480 A1 | 1/2014 |
| JP | H10-503383 A | 3/1998 |
| JP | 2006-129727 A | 5/2006 |
| JP | 2014-533934 A | 12/2014 |
| WO | 2012/121225 A1 | 9/2012 |
| WO | 2013-053855 A1 | 4/2013 |

OTHER PUBLICATIONS

Grady et al. (Analytical Biochemistry vol. 173, Issue 1, Aug. 15, 1988, pp. 111-115. (Year: 1988).*
Biological Buffers AppliChem 2008, pp. 1-16 (Year: 2008).*
International Search Report issued in International Application No. PCT/JP2016/063648; dated Jul. 19, 2016 (2 pages).
Notomi et. al, "Loop-mediated isothermal amplification of DNA", Nucleic Acids Research, 2000, vol. 28, No. 12 (7 pages).
Mitani et. al, "Rapid SNP diagnostics using asymmetric isothermal amplification and a new mismatch-suppression technology", Nature Methods, vol. 4, No. 3, Mar. 2007, pp. 257-262 (6 pages).
PCR, RT-PCR no Seikoritsu o Takameru Tameni, [online], 2011.8, [retrieval date Jun. 30, 2016 (Jun. 30, 2016)], Internet: <URL: https://www.qiagen.com/jp/resources/resourcedetail?id=86cb37aa-32f5-4989-a2aa-c741fdb853fd&lang=ja-jp>, p. 6, fig. 6 (22 pages).

* cited by examiner

*Primary Examiner* — Jezia Riley
(74) *Attorney, Agent, or Firm* — Osha Bergman Watanabe & Burton LLP

(57) ABSTRACT

A method for producing a dry reagent composition includes preparing a reagent solution including a Good's buffer in a concentration of more than 2.5 mM, an ammonium salt, a drying protection agent, and a nucleic acid amplification enzyme, and drying the reagent solution. A method for suppressing a decrease in enzyme activity during drying includes adding a Good's buffer in a biochemical reagent comprising an ammonium salt and an enzyme prior to drying the enzyme.

12 Claims, No Drawings

Specification includes a Sequence Listing.

SEQUENCE LISTING

```
<160> NUMBER OF SEQ ID NOS: 5

<210> SEQ ID NO 1
<211> LENGTH: 36
<212> TYPE: DNA
<213> ORGANISM: Artificial
<220> FEATURE:
<223> OTHER INFORMATION: primer 1

<400> SEQUENCE: 1
cttatataat tataaggaat gcaatcaggt cgtttc                                36

<210> SEQ ID NO 2
<211> LENGTH: 35
<212> TYPE: DNA
<213> ORGANISM: Artificial
<220> FEATURE:
<223> OTHER INFORMATION: primer 2

<400> SEQUENCE: 2
cccgaaaatg agacaccgat ttaatcgcaa cacgc                                 35

<210> SEQ ID NO 3
<211> LENGTH: 21
<212> TYPE: DNA
<213> ORGANISM: Artificial
<220> FEATURE:
<223> OTHER INFORMATION: primer 3

<400> SEQUENCE: 3
agatatagca tacccagggt c                                                21

<210> SEQ ID NO 4
<211> LENGTH: 13
<212> TYPE: DNA
<213> ORGANISM: Artificial
<220> FEATURE:
<223> OTHER INFORMATION: primer 4

<400> SEQUENCE: 4
aaaccgtcct gcc                                                         13

<210> SEQ ID NO 5
<211> LENGTH: 13
<212> TYPE: DNA
<213> ORGANISM: Artificial
<220> FEATURE:
```

```
<223> OTHER INFORMATION: primer 5

<400> SEQUENCE: 5
gttcgcgcca gtg                                                          13
```

ENZYME REACTION REAGENT HAVING DRIED FORM AND METHOD FOR PREPARING THE SAME

TECHNICAL FIELD

One or more embodiments of the present invention relate to a method for preserving a protein and a reagent used therefor.

BACKGROUND

In recent years, there have been developed various test methods and diagnostic methods, in which the high specificity of enzyme reaction have been utilized, and some of these methods have already been distributed as products over the world. In general, since an enzyme reaction solution has a complicated composition consisting of a buffer, metal salts, a substrate, a coenzyme, etc., preparing such a reaction solution at the time of performing a test or a diagnosis is complicated. Hence, in order to simplify the preparation of such a reaction solution, there is a method of pre-mixing reagents that are necessary for the reaction. A premix reagent having a liquid form can be used only by adding a specimen thereto, and thus, it has high simplicity. However, when the premix reagent is preserved in the form of a diluted solution for a long period of time, its enzyme activity can be deteriorated in many cases. Such a premix reagent with a liquid form has a quality assurance period of about 1 year at a low temperature. On the other hand, a premix reagent having a dried form needs to be dissolved when used. However, such a premix reagent solution for re-dissolving can be used in a wide variety of applications, since the type or volume of a solution for dissolving it can be selected according to needs. In addition, a premix reagent with a dried form is lightweight and thus, is easily transported, and it can be stably preserved at normal temperature for a long period of time.

A well-known enzyme reaction is a sequence-specific nucleic acid synthesis reaction using polymerase. Nucleic acid amplification methods including PCR as a typical example utilize this reaction, and this sequence-specific nucleic acid synthesis reaction has been utilized not only in academic research institutes, but also for genetic testing and other applications. Some genetic testing reagents are capable of starting the reaction only by adding a specimen thereto. Some dry reagents can be stably preserved at room temperature for a long period of time.

Nucleic acid amplification reaction systems often comprise ammonium salts, in order to optimize the reactions. For instance, Bst DNA polymerase, Aac DNA polymerase, and the like, which are used in isothermal amplification methods such as a LAMP method or a SmartAmp method, generally comprise ammonium sulfate in the reaction solution (Non Patent Literatures 1 and 2).

However, it has been previously known that, if a reagent comprising such ammonium salts is freeze-dried, the enzyme activity of a reaction solution obtained by re-dissolving the reagent is significantly reduced, even though the re-dissolving takes place immediately after drying the reagent. There has been proposed a method which comprises freeze-drying the reagent in a state in which an enzyme and a buffer or a component thereof are not allowed to come into contact with ammonium salts, or they are not allowed to come into contact with ammonium salts at high concentrations, and then mixing them with one another upon reacting them (Patent Literature 1). However, the separation of the components until the reaction is likely to have restriction in product form. An ammonium salt-containing enzyme reaction reagent having a dried form, which does not need the separation of the components until the reaction, has not yet been known.

Patent Literature

Patent Literature 1: JP Patent Publication No. 2006-129727 A

Non Patent Literature

Non Patent Literature 1: Notomi et. al., Nucleic Acids Res., 28, 2000, e63

Non Patent Literature 2: Mitani et. al., Nat. Methods, 4, 2007, 257-262

SUMMARY

One or more embodiments of the present invention provide an ammonium salt-containing enzyme reaction reagent having a dried form, which does not need supplementation of components into the reaction system upon performing the reaction and can be stably preserved at room temperature.

The inventors have conducted intensive studies and have found that a decrease in enzyme activity, which occurs when a reagent containing an ammonium salt is dried and re-dissolved, can be suppressed by using a Good's buffer.

One or more embodiments of the present invention include the following features.

(1) Use of a Good's buffer for suppressing a decrease in enzyme activity during drying, in a biochemical reagent consisting of, at least, a buffer, an ammonium salt, and an enzyme.

(2) A method for producing a dry reagent composition, comprising:

a) a step of preparing a reagent solution comprising a Good's buffer with a concentration of more than 2.5 mM, an ammonium salt, a drying protection agent, and a nucleic acid amplification enzyme, and b) a step of drying the reagent solution prepared in the step a).

(3) The method according to the above (2), wherein the concentration of the Good's buffer is 5 mM or more.

(4) The method according to the above (2) or (3), wherein the Good's buffer is at least one selected from the group consisting of BES, Bicine, CHES, DIPSO, EPPS, HEPES, HEPPSO, MOPS, POPSO, TAPS, TAPSO, TES, and Tricine.

(5) The method according to any one of the above (2) to (4), wherein the Good's buffer is at least one selected from the group consisting of BES, Bicine, HEPES, HEPPSO, POPSO, and Tricine.

(6) The method according to any one of the above (2) to (5), wherein the Good's buffer is Bicine or Tricine.

(7) The method according to any one of the above (2) to (6), wherein the ammonium salt is ammonium sulfate.

(8) The method according to any one of the above (2) to (7), wherein the drying protection agent is at least one selected from the group consisting of a sugar, a surfactant, a water-soluble polymer, and a protein.

(9) A dry reagent composition for use in a nucleic acid amplification reaction, which is obtained by the method according to any one of the above (2) to (8).

The present description includes part or all of the contents as disclosed in Japanese Patent Application No. 2015-095535, which is a priority document of the present application.

One or more embodiments of the present invention provide an ammonium salt-containing enzyme reaction reagent having a dried form, which does not need supplementation of components into the reaction system upon performing the reaction and can be stably preserved at room temperature.

DETAILED DESCRIPTION OF EMBODIMENTS

Among buffers, the Good's buffer used in one or more embodiments of the present invention particularly indicates a buffer comprising a compound having a zwitterionic structure in a molecule thereof, and the characteristic properties of the Good's buffer include chemical stability, acid dissociation equilibrium that is hardly affected by ionic composition, and low ability to form a complex with metal ions. Any Good's buffer exhibiting properties similar to said characteristic properties may be used.

The Good's buffer used in one or more embodiments of the present invention may be at least one selected from the group consisting of BES (N,N-Bis(2-hydroxyethyl)-2-aminoethanesulfonic acid), Bicine (N,N-Bis(2-hydroxyethyl)glycine), CHES (N-Cyclohexyl-2-aminoethanesulfonic acid), DIPSO (3-[N,N-Bis(2-hydroxyethyl)amino]-2-hydroxy-1-propanesulfonic acid), EPPS (3-[4-(2-Hydroxyethyl)-1-piperazinyl]propanesulfonic acid), HEPES (2-[4-(2-Hydroxyethyl)-1-piperazinyl]ethanesulfonic acid), HEPPSO (2-Hydroxy-3-[4-(2-hydroxyethyl)-1-piperazinyl]propanesulfonic acid), MOPS (3-Morpholinopropanesulfonic acid), POPSO (Piperazine-1,4-bis(2-hydroxy-3-propanesulfonic acid), TAPS (N-Tris(hydroxymethyl)methyl-3-aminopropanesulfonic acid), TAPSO (2-Hydroxy-N-tris(hydroxymethyl)methyl-3-aminopropanesulfonic acid), TES (N-Tris(hydroxymethyl)methyl-2-aminoethanesulfonic acid), and Tricine (N-[Tris(hydroxymethyl)methyl]glycine). The Good's buffer may be at least one selected from the group consisting of BES, Bicine, HEPES, HEPPSO, POPSO, and Tricine, or it may be Bicine or Tricine. The Good's buffer used in one or more embodiments of the present invention can have various forms such as a hydrate or salts. For example, as HEPPSO, 2-Hydroxy-3-[4-(2-hydroxyethyl)-1-piperazinyl]propanesulfonic acid or a monohydrate can be used, and as POPSO, Piperazine-1,4-bis(2-hydroxy-3-propanesulfonic acid or a dihydrate can be used.

The concentration of the Good's buffer used in one or more embodiments of the present invention may be more than 2.5 mM. It may be 5 mM or more. By setting the concentration of the Good's buffer to be the aforementioned value, buffer effects sufficient for maintaining enzyme activity can be obtained. On the other hand, if the concentration value is less than 2.5 mM, it is likely that buffer effects sufficient for maintaining enzyme activity cannot be obtained. In such a case, in order to recover the enzyme activity, a reagent may need to be added before performing the reaction. However, in a nucleic acid amplification reaction, for example, such a step of adding a reagent is highly likely to increase a risk of contamination. In addition, addition of a step leads to an increase in production costs.

Moreover, the concentration of the Good's buffer used in one or more embodiments of the present invention may be 125 mM or less. The concentration exceeding 125 mM may affect an enzyme reaction.

The pH of the Good's buffer used in one or more embodiments of the present invention varies depending on the type of an enzyme used, and it is not particularly limited, as long as it is in the buffering range of each of the above described buffers. The pH of the present Good's buffer may be pH 7.0 or more, pH 7.5 or more, or pH 8.0 or more, and also, it may be pH 10.0 or less, pH 9.5 or less, or pH 9.0 or less. Specifically, it may be pH 7.0 to 10.0, pH 7.5 to 9.5, or pH 8.0 to 9.0.

The ammonium salt used in one or more embodiments of the present invention may be ammonium benzoate, ammonium chloride, ammonium formate, triammonium citrate, diammonium hydrogen citrate, ammonium dihydrogen citrate, ammonium acetate, ammonium bromide, ammonium tartrate, ammonium nitrate, ammonium oxalate, ammonium thiocyanate, ammonium sulfate, diammonium hydrogen phosphate, ammonium dihydrogen phosphate or other ammonium salts, and it may be ammonium sulfate.

The concentration of the ammonium salt used in one or more embodiments of the present invention is not particularly limited. It may be 1 mM or more, 2 mM or more, or 5 mM or more, and also, it may be 50 mM or less, 40 mM or less, or 25 mM or less. Specifically, it may be 1 to 50 mM, 2 to 40 mM, or 5 to 25 mM. If the concentration of the ammonium salt is out of this numerical range, it is likely that the effect of improving enzyme activity cannot be sufficiently obtained.

The enzyme used in one or more embodiments of the present invention is not particularly limited. Any enzyme whose activity is likely to be decreased in the presence of an ammonium salt, when it is dried, may be used. An example of the present enzyme includes a nucleic acid amplification enzyme used in nucleic acid amplification reactions such as PCR or an isothermal amplification method. Specific examples of the enzyme used in one or more embodiments of the present invention include DNA polymerase such as Aac DNA polymerase, Bst DNA polymerase, Pfu DNA polymerase, T4 DNA polymerase, Taq DNA polymerase, Tfl DNA polymerase, or Tth DNA polymerase. It is to be noted that these nucleic acid amplification enzymes may have reverse transcription ability.

The concentration of the enzyme used in one or more embodiments of the present invention is not particularly limited, as long as a reaction of interest progresses. For example, in a nucleic acid amplification reaction, the concentration of the enzyme may be 0.01 U or more and 100 U or less, 0.1 U or more and 50 U or less, or 1 U or more and 10 U or less.

In the biochemical reagent used in one or more embodiments of the present invention that is in a non-dried state, the concentration of a Good's buffer, the pH of a Good's buffer, the concentration of an ammonium salt, and the concentration of an enzyme may be each selected from the above described ranges. Likewise, in a reaction solution prepared by the step of preparing a reagent solution used in one or more embodiments of the present invention, the concentration of a Good's buffer, the pH of a Good's buffer, the concentration of an ammonium salt, and the concentration of an enzyme may be each selected from the above described ranges.

The biochemical reagent used in one or more embodiments of the present invention may be a reagent used to perform a nucleic acid amplification reaction using polymerase, a ligation reaction using ligase, an antibody-antigen reaction, a phosphorylation reaction using kinase, an alkylation reaction using alkyl transferase, a nucleic acid decomposition reaction using nuclease, a DNA homologous recombination reaction, and a protein decomposition reaction using protease, and it may be a reagent used to perform a nucleic acid amplification reaction using polymerase.

The step of preparing a reagent solution in one or more embodiments of the present invention is a step of dissolving a Good's buffer, an ammonium salt, a drying protection agent and a nucleic acid amplification enzyme in a solvent. The solvent may be water, and the water may be distilled water or deionized water, and it may be sterilized distilled water or sterilized deionized water. The present step is generally carried out at a low temperature. The temperature applied in the present step may be adjusted a low temperature, or a space such as the inside of a room in which the step is carried out may also be adjusted to a low temperature.

The drying step in one or more embodiments of the present invention may be carried out by means such as vacuum drying, freeze-drying, hot-air drying or spray drying. Freeze-drying may be used in one or more embodiments. In the freeze-drying, a common freeze-drying apparatus may be used, and drying conditions can be determined, as appropriate. Moreover, pre-freezing may also be carried out, as necessary.

In one or more embodiments of the present invention, a decrease in enzyme activity means that the activity of an enzyme in a solution prepared by drying and then re-dissolving decreases in comparison to the activity of the enzyme in a solution before drying. One of the causes of such a decrease in enzyme activity may be the pH of a reaction solution that is largely changed from the optimal pH of the enzyme, when a reagent comprising a commonly used Tris-HCl buffer and an ammonium salt is dried and is then re-dissolved in a solution. However, the cause thereof is not particularly limited.

There are various methods of measuring the activity of an enzyme, depending on the type of each enzyme. A measurement method suitable for the used enzyme may be selected, as appropriate.

For example, in a nucleic acid amplification reaction, a Ct (Threshold Cycle) value that is the number of cycles when a PCR amplification product has reached a certain amount, or a Tt (Threshold Time) value that is a time when the amplification product of an isothermal amplification reaction has reached a certain amount, can be used to measure the activity of an enzyme.

These values can be obtained by monitoring, in real time, the amplification product, using fluorescent nucleic acid intercalators such as SYBR Green or fluorescent nucleic acid probes such as a Taqman probe.

The dry composition according to one or more embodiments of the present invention needs the removal of a water content from a biochemical reagent by the above-described drying method, and then, addition of water when a reaction of interest is carried out. The water added herein includes pure water, a buffer, a salt solution, a protein solution, and an organic solvent.

For the purpose of more strongly retaining enzyme activity, the dry composition according to one or more embodiments of the present invention may comprise a drying protection agent. The drying protection agent used herein includes a sugar, a surfactant, a water-soluble polymer, and a protein.

Examples of the sugar that can be used herein include a monosaccharide, a disaccharide, a trisaccharide, a lower oligosaccharide, a polysaccharide, and a derivative thereof. Examples include: monosaccharides such as arabinose or glucose; monosaccharide derivatives such as sorbitol or mannitol; reducing disaccharides such as cellobiose, maltose, or lactose; non-reducing disaccharides such as sucrose or trehalose; trisaccharides such as raffinose or maltotriose; lower oligosaccharides such as maltotetraose, maltopentaose, or maltohexaose; and polysaccharides such as dextran. Examples include arabinose, sucrose, cellobiose, dextran, trehalose, maltose, maltotriose, lactose, and raffinose.

Examples of the surfactant include NP-40 (Nonidet P-40, (octylphenoxy)polyethoxyethanol), Tween 20 (Polysorbate 20, polyoxyethylene sorbitan monolaurate), Triton X-100 (poly(oxyethylene)octylphenyl ether), water-soluble polymers such as Ficoll or polyethylene glycol, and proteins such as bovine serum albumin Any types of drying protection agents can be mixed with one another at any ratio, and the drying protection agent is not limited to the scope of the Examples.

The drying protection agent may be added into the dry composition in an amount of 1 (w/v) % or more, or 2.5 (w/v) % or more, and also in an amount of 30 (w/v) % or less, or 20 (w/v) % or less. Specifically, the added amount of the drying protection agent may be 1 to 30 (w/v) %, or 2.5 to 20 (w/v) %. If the added amount of the drying protection agent is smaller than this numerical value range, it is likely that the effect of maintaining sufficient enzyme activity cannot be obtained. In contrast, if it is greater than this numerical value range, it is likely that the enzyme activity is inhibited.

EXAMPLES

Hereinafter, one or more embodiments of the present invention will be specifically described in the following examples. However, these examples are not intended to limit the scope of the present invention. It is to be noted that the reagents used herein have been purchased from Wako Pure Chemical Industries, Ltd., unless otherwise specified.

Example 1

A solution comprising a 20 mM Good's buffer, 10 mM potassium chloride, 10 mM ammonium sulfate (manufactured by Nacalai Tesque, Inc.), 8 mM magnesium sulfate (manufactured by Kanto Chemical Co., Inc.), 1.4 mM deoxynucleotide triphosphate (manufactured by NIPPON GENE CO., LTD.), and 5% trehalose (manufactured by Nacalai Tesque, Inc.) in 1 mL of deionized water was prepared. As such Good's buffers, BES, Bicine, DIPSO (manufactured by SIGMA-ALDRICH), EPPS, HEPES (manufactured by GIBCO Laboratories), HEPPSO, MOPS, POPSO, TAPS, TAPSO (manufactured by SIGMA-ALDRICH), TES (manufactured by Nacalai Tesque, Inc.) and Tricine (manufactured by Nacalai Tesque, Inc.), which had been adjusted to pH 8.0 with NaOH, and CHES adjusted to pH 8.8, were used. This solution was pre-frozen at −40° C. for 1 hour, and the pressure was reduced to 10 Pa or less. Then, the solution was freeze-dried at −40° C. for 7 hours, at −10° C. for 12 hours, at 10° C. for 3 hours, and at 25° C. for 1 hour, using a freeze-dryer (1-DU-2110 model and DRC-1000 model, manufactured by Tokyo Rikakikai Co., Ltd.). After completion of the drying, each dried reagent was dissolved in deionized water, and the pH thereof was then measured using a pH meter. Thereafter, the obtained value was compared with the value before drying. The amount of the deionized water upon re-dissolving was 1 mL. The results are shown in Table 1. The pH change value indicates a difference obtained by subtracting the pH value before drying from the pH value after drying.

TABLE 1

|  | BES | Bicine | DISPO | EPPS | HEPES |
|---|---|---|---|---|---|
| pH change value | −0.47 | −0.39 | −0.42 | −0.38 | −0.45 |

|  | HEPPSO | MOPS | POPSO | TAPS | TAPSO |
|---|---|---|---|---|---|
| pH change value | −0.39 | −0.4 | −0.33 | −0.76 | −0.48 |

|  | TES | Tricine | Tris (8.0) | CHES | Tris (8.8) |
|---|---|---|---|---|---|
| pH change value | −0.46 | −0.41 | −0.85 | −0.97 | −1.18 |

Comparative Example 1

A freeze-dried reagent was prepared under the same conditions as those applied in Example 1, with the exception that a Tris buffer adjusted to pH 8.0 or pH 8.8 with HCl (manufactured by Nacalai Tesque, Inc.) was used instead of the Good's buffer. These dried reagents were each dissolved in deionized water, and the pH thereof was then measured using a pH meter. The obtained value was compared with the value before drying. The results are shown in Table 1.

As shown in Table 1, when the Good's buffers were used, clear inhibition of the pH value change was observed in comparison to the case of using the Tris buffer.

Example 2

A solution comprising a 20 mM Good's buffer, 10 mM potassium chloride, 10 mM ammonium sulfate (manufactured by Nacalai Tesque, Inc.), 8 mM magnesium sulfate (manufactured by Kanto Chemical Co., Inc.), 1.4 mM deoxynucleotide triphosphate (manufactured by NIPPON GENE CO., LTD.), 1.6 µM primer 1 (SEQ ID NO: 1), 1.6 µM primer 2 (SEQ ID NO: 2), 0.8 µM primer 3 (SEQ ID NO: 3), 0.2 µM primer 4 (SEQ ID NO: 4), 0.2 µM primer 5 (SEQ ID NO: 5), 4U Bst DNA polymerase (manufactured by NIPPON GENE CO., LTD.), and 5% trehalose (manufactured by Nacalai Tesque, Inc.) in 25 µL of deionized water was prepared. As such Good's buffers, Bicine, HEPES (manufactured by GIBCO Laboratories), HEPPSO, POPSO, TAPS, TAPSO (manufactured by SIGMA-ALDRICH), TES (manufactured by Nacalai Tesque, Inc.) and Tricine (manufactured by Nacalai Tesque, Inc.), which had been adjusted to pH 8.0 with NaOH, and CHES adjusted to pH 8.8, were used. This solution was pre-frozen at −40° C. for 1 hour, and the pressure was reduced to 10 Pa or less. Then, the solution was freeze-dried at −40° C. for 7 hours, at −10° C. for 12 hours, at 10° C. for 3 hours, and at 25° C. for 1 hour, using a freeze-dryer (1-DU-2110 model and DRC-1000 model, manufactured by Tokyo Rikakikai Co., Ltd.). After completion of the drying, each dried reagent was dissolved in deionized water, a template (1 ng) was then added thereto, and the obtained mixture was then incubated at 63° C. for 60 minutes. The amount of the deionized water upon re-dissolving was 25 µL. The reaction was pursued using a real-time fluorescence measurement device (LightCycler 96, manufactured by ROCHE). The Tt value used as a scale of reaction speed was calculated using LightCycler Software. The obtained Tt value was compared with the value obtained before drying. The results are shown in Table 2. The Tt change value indicates a difference obtained by subtracting the Tt value before drying from the Tt value after drying in each Good's buffer.

TABLE 2

|  | Bicine | HEPES | HEPPSO | POPSO | TAPS | TAPSO |
|---|---|---|---|---|---|---|
| Tt change value | 3.92 | 6.49 | 3.39 | 3.24 | 20.14 | 8.91 |

|  | TES | Tricine | Tris (8.0) | CHES | Tris (8.8) |
|---|---|---|---|---|---|
| Tt change value | 8.52 | 5.69 | 24.11 | 5.25 | 17.2 |

Comparative Example 2

A freeze-dried reagent was prepared under the same conditions as those applied in Example 2, with the exception that a Tris buffer adjusted to pH 8.0 or pH 8.8 with HCl (manufactured by Nacalai Tesque, Inc.) was used instead of the Good's buffer. These dried reagents were each dissolved in deionized water, a template (1 ng) was then added thereto, and the obtained mixture was then incubated at 63° C. for 60 minutes. Thereafter, the reaction was pursued using a real-time fluorescence measurement device (LightCycler 96, manufactured by ROCHE). The Tt value used as a scale of reaction speed was calculated using LightCycler Software. The obtained Tt value was compared with the value obtained before drying. The results are shown in Table 2.

As shown in Table 2, when the Good's buffers were used, clear inhibition of the Tt value change was observed in comparison to the case of using the Tris buffer.

Example 3

A solution comprising 5 to 40 mM Tricine-NaOH (pH 8.0, each concentration is shown in the following table), 10 mM potassium chloride, 10 mM ammonium sulfate (manufactured by Nacalai Tesque, Inc.), 8 mM magnesium sulfate (manufactured by Kanto Chemical Co., Inc.), 1.4 mM deoxynucleotide triphosphate (manufactured by NIPPON GENE CO., LTD.), 1.6 µM primer 1 (SEQ ID NO: 1), 1.6 µM primer 2 (SEQ ID NO: 2), 0.8 µM primer 3 (SEQ ID NO: 3), 0.2 µM primer 4 (SEQ ID NO: 4), 0.2 µM primer 5 (SEQ ID NO: 5), 4 U Bst DNA polymerase (manufactured by NIPPON GENE CO., LTD.), and 5% trehalose (manufactured by Nacalai Tesque, Inc.) in 25 µL of deionized water was prepared. This solution was pre-frozen at −40° C. for 1 hour, and the pressure was reduced to 10 Pa or less. Then, the solution was freeze-dried at −40° C. for 7 hours, at −10° C. for 12 hours, at 10° C. for 3 hours, and at 25° C. for 1 hour, using a freeze-dryer (FDU-2110 model and DRC-1000 model, manufactured by Tokyo Rikakikai Co., Ltd.). After completion of the drying, each dried reagent was dissolved in deionized water, a template (1 ng) was then added thereto, and the obtained mixture was then incubated at 63° C. for 60 minutes. The amount of the deionized water upon re-dissolving was 25 µL. The reaction was pursued using a real-time fluorescence measurement device (LightCycler 96, manufactured by ROCHE). The Tt value used as a scale of reaction speed was calculated using LightCycler Software. The obtained Tt value was compared with the value obtained before drying. The results are shown in Table 3. The Tt change value was calculated in the same manner as that in Example 2.

TABLE 3

| | 40 mM | 20 mM | 10 mM | 5 mM | 2.5 mM | 1 mM |
|---|---|---|---|---|---|---|
| Tt change value | 3.92 | 5.11 | 5.37 | 8.34 | 20 or more | 20 or more |

Comparative Example 3

A freeze-dried reagent was prepared under the same conditions as those applied in Example 3, with the exception of using 2.5 mM or 1 mM Tricine-NaOH. These dried reagents were each dissolved in deionized water, a template (1 ng) was then added thereto, and the obtained mixture was then incubated at 63° C. for 60 minutes. Thereafter, the reaction was pursued using a real-time fluorescence measurement device (LightCycler 96, manufactured by ROCHE). The Tt value used as a scale of reaction speed was calculated using LightCycler Software. The obtained Tt value was compared with the value obtained before drying. The results are shown in Table 3.

As shown in Table 3, when Tricine-NaOH has a concentration of more than 2.5 mM, the enzyme activity can be maintained in one or more embodiments of the present invention.

All publications, patents and patent applications cited in the present description are incorporated herein by reference in their entirety.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A method for producing a dry reagent composition, comprising:

preparing a reagent solution comprising a Good's buffer in a concentration of more than 2.5 mM, an ammonium salt, a drying protection agent, and a nucleic acid amplification enzyme, and drying the reagent solution, wherein the Good's buffer is at least one selected from the group consisting of N,N-bis(2-hydroxyethyl)-2-aminoethanesulfonic acid (BES), N,N-bis(2-hydroxyethyl) glycine (Bicine), N-cyclohexyl-2-aminoethanesulfonic acid (CHES), 3-[N,N-bis(2-hydroxyethyl)amino]-2-hydroxy-1-propanesulfonic acid (DIPSO), 3-[4-(2-hydroxyethyl)-1-piperazinyl]propanesulfonic acid (EPPS), 2-[4-(2-hydroxyethyl)-1-piperazinyl]ethanesulfonic acid (HEPES), 2-hydroxy-3-[4-(2-hydroxyethyl)-1-piperazinyl]propanesulfonic acid (HEPPSO), 3-morpholinopropanesulfonic acid (MOPS), piperazine-1,4-bis(2-hydroxy-3-propanesulfonic acid (POPSO), 2-hydroxy-N-tris(hydroxymethyl)methyl-3-aminopropanesulfonic acid (TAPSO), N-tris(hydroxymethyl)methyl-2-aminoethanesulfonic acid (TES), and N-[tris(hydroxymethyl)methyl]glycine (Tricine).

2. The method according to claim 1, wherein the concentration of the Good's buffer is 5 mM or more.

3. The method according to claim 1, wherein the Good's buffer is at least one selected from the group consisting of BES, Bicine, HEPES, HEPPSO, POPSO, and Tricine.

4. The method according to claim 3, wherein the Good's buffer is Bicine or Tricine.

5. The method according to claim 1, wherein the ammonium salt is ammonium sulfate.

6. The method according to claim 1, wherein the drying protection agent is at least one selected from the group consisting of a sugar, a surfactant, a water-soluble polymer, and a protein.

7. The dry reagent composition produced by the method according to claim 1, wherein the dry reagent composition is used in a nucleic acid amplification reaction.

8. A method for suppressing a decrease in enzyme activity during drying, the method comprising adding a Good's buffer in a biochemical reagent comprising an ammonium salt and an enzyme prior to drying the enzyme.

9. The method according to claim 8, wherein the Good's buffer is added in a concentration of 2.5 mM or more.

10. The method according to claim 8, wherein the Good's buffer is at least one selected from the group consisting of N,N-bis(2-hydroxyethyl)-2-aminoethanesulfonic acid (BES), N,N-bis(2-hydroxyethyl)glycine (Bicine), N-cyclohexyl-2-aminoethanesulfonic acid (CHES), 3-[N,N-bis(2-hydroxyethyl)amino]-2-hydroxy-1-propanesulfonic acid (DIPS 0), 3-[4-(2-hydroxyethyl)-1-piperazinyl]propanesulfonic acid (EPPS), 2-[4-(2-hydroxyethyl)-1-piperazinyl]ethanesulfonic acid (HEPES), 2-hydroxy-3-[4-(2-hydroxyethyl)-1-piperazinyl]propanesulfonic acid (HEPPSO), 3-morpholinopropanesulfonic acid (MOPS), piperazine-1,4-bis (2-hydroxy-3-propanesulfonic acid (POPSO), N-tris(hydroxymethyl)methyl-3-aminopropanesulfonic acid (TAPS), 2-hydroxy-N-tris(hydroxymethyl)methyl-3-aminopropanesulfonic acid (TAPSO), N-tris(hydroxymethyl)methyl-2-aminoethanesulfonic acid (TES), and N-[tris(hydroxymethyl)methyl]glycine (Tricine).

11. The method according to claim 8, wherein the ammonium salt is ammonium sulfate.

12. The method according to claim 8, wherein the biochemical reagent further comprises a drying protection agent selected from the group consisting of a sugar, a surfactant, a water-soluble polymer, and a protein.

* * * * *